(12) United States Patent
Engqvist (10) Patent No.: US 10,292,791 B2
(45) Date of Patent: May 21, 2019

(54) CEMENT SYSTEMS, HARDENED CEMENTS AND IMPLANTS

(71) Applicant: Psilox AB, Uppsala (SE)

(72) Inventor: Håkan Engqvist, Östhammar (SE)

( * ) Notice: Subject to any disclaimer, the term of this patent is extended or adjusted under 35 U.S.C. 154(b) by 56 days.

(21) Appl. No.: 15/324,314

(22) PCT Filed: Jul. 7, 2015

(86) PCT No.: PCT/IB2015/001800
§ 371 (c)(1),
(2) Date: Jan. 6, 2017

(87) PCT Pub. No.: WO2016/005822
PCT Pub. Date: Jan. 14, 2016

(65) Prior Publication Data
US 2017/0165034 A1 Jun. 15, 2017

(30) Foreign Application Priority Data

Jul. 7, 2014 (SE) ...................... 1400345

(51) Int. Cl.
*A61C 8/00* (2006.01)
*A61K 6/06* (2006.01)
(Continued)

(52) U.S. Cl.
CPC .............. *A61C 8/0015* (2013.01); *A61C 5/73* (2017.02); *A61C 13/09* (2013.01); *A61K 6/0606* (2013.01);
(Continued)

(58) Field of Classification Search
CPC ......... A61C 8/0015; A61C 5/73; A61C 13/09; A61K 6/0606; A61K 6/0631;
(Continued)

(56) References Cited

U.S. PATENT DOCUMENTS 5,063,257 A * 11/1991 Akahane .............. A61K 6/0835
522/120
5,147,904 A * 9/1992 Jochum ................. A61L 27/446
521/79
(Continued)

FOREIGN PATENT DOCUMENTS

EP 559 627 A2 9/1993
WO 90/11066 A1 10/1990
(Continued)

OTHER PUBLICATIONS

Azam et al, Archives of Orofacial Sciences, 8(2):54-59 (Oct. 31, 2013).
Chemical Abstract 1990:42487.

*Primary Examiner* — Nicholas D Lucchesi
(74) *Attorney, Agent, or Firm* — Porter Wright Morris & Arthur LLP (57) ABSTRACT

A cement system for forming an implant comprises a reactive glass ionomer cement (GIC) powder, a polycarboxylic acid or salt, and a filler. The polycarboxylic acid or salt is included to initially provide a paste having a pH less than 7 when the cement system is mixed with water. In one embodiment, the filler is substantially inert when mixed with water and is selected from $(CaO)(Al_2O_3)6$, $(CaO)(Al_2O_3)_2$, calcium silicate $(CaOSiO_2)$, and mixtures thereof. In another embodiment, the filler is substantially reactive when mixed with water and is selected from $(CaO)_2(SiO_2)$, $(CaO)_3(SiO_2)$, and mixtures thereof, and the cement system includes an additional acid to maintain the paste at a pH less than 7 for at least one hour after the cement system is mixed with water.

29 Claims, 11 Drawing Sheets (51) Int. Cl.
*A61C 5/73* (2017.01)
*A61C 13/09* (2006.01)
*A61K 6/083* (2006.01)
*C04B 14/04* (2006.01)
*C04B 14/36* (2006.01)
*C04B 28/04* (2006.01)
*C04B 111/00* (2006.01)

(52) U.S. Cl.
CPC .......... *A61K 6/0612* (2013.01); *A61K 6/0631* (2013.01); *A61K 6/0675* (2013.01); *A61K 6/0835* (2013.01); *C04B 14/043* (2013.01); *C04B 14/36* (2013.01); *C04B 28/04* (2013.01); *C04B 2111/00836* (2013.01)

(58) Field of Classification Search
CPC .. A61K 6/0675; A61K 6/0835; C04B 14/043; C04B 14/36; C04B 28/04; C04B 2111/00836
See application file for complete search history.

(56) References Cited

U.S. PATENT DOCUMENTS

| | | | |
|---|---|---|---|
| 5,369,142 A * | 11/1994 | Culbertson | A61K 6/0017 523/116 |
| 7,531,035 B2 | 5/2009 | Hermansson et al. | |
| 7,699,925 B2 | 4/2010 | Engqvist et al. | |
| 7,867,329 B2 | 1/2011 | Hermansson et al. | |
| 7,972,434 B2 | 7/2011 | Engqvist et al. | |
| 9,205,035 B2 | 12/2015 | Engqvist et al. | |
| 2003/0121454 A1 * | 7/2003 | Hermansson | C04B 28/06 106/692 |
| 2003/0167967 A1 * | 9/2003 | Narhi | A61K 6/0017 106/35 |
| 2006/0037514 A1 | 2/2006 | Hermansson et al. | |
| 2006/0102053 A1 | 5/2006 | Engqvist et al. | |
| 2006/0167148 A1 | 7/2006 | Engqvist et al. | |
| 2007/0254998 A1 | 11/2007 | Orlowski et al. | |
| 2008/0058442 A1 * | 3/2008 | Hermansson | A61K 6/0835 523/115 |
| 2008/0242760 A1 * | 10/2008 | van den Bosch | A61K 6/0017 523/116 |
| 2009/0050015 A1 * | 2/2009 | Hermansson | A61L 24/02 106/35 |
| 2012/0189987 A1 * | 7/2012 | Hermansson | A61K 6/0205 433/228.1 |
| 2015/0111172 A1 * | 4/2015 | Jung | A61C 13/0003 433/172 |

FOREIGN PATENT DOCUMENTS

| | | |
|---|---|---|
| WO | 00/21489 A1 | 4/2000 |
| WO | 01/76534 A1 | 10/2001 |
| WO | 01/76535 A1 | 10/2001 |
| WO | 2003/041662 A1 | 5/2003 |
| WO | 2004/037215 A1 | 5/2004 |
| WO | 2005/039508 A1 | 5/2005 |
| WO | 2009/025599 A1 | 2/2009 |

\* cited by examiner

CEMENT SYSTEMS, HARDENED CEMENTS AND IMPLANTS

FIELD OF THE INVENTION

The present invention is directed to cement systems comprising glass ionomer cement (GIC) powder and ceramic filler powder. In one embodiment, the filler is substantially inert when mixed with water and, in another embodiment, the filler is substantially reactive when mixed with water. The present invention is also directed to hardened cements formed by mixing the cement systems with water, and to dental implants formed of the hardened cements. In specific embodiments, the ceramic filler provides hardened cements with bioactive properties.

BACKGROUND OF THE INVENTION

The present invention relates to cement systems that combine a hydrating cement system, and more particularly cement-based systems that comprise chemically bonded ceramics of calcium aluminates and/or calcium silicates, and traditional glass ionomer cement materials. The inventive systems are suitable for use as biomaterials, for example, as implants and, in a specific embodiment, as implants in dental applications.

Materials such as dental materials and other implants desirably interact with the human body and therefore should be as bioactive or biocompatible as possible. Other properties that are specifically required for dental cement materials include good handling ability with simple applicability, molding ability that permits good shaping, hardening/solidification that is sufficiently rapid for use within minutes, especially without detrimental heat generation, and that provides serviceability directly following therapy, corrosion resistance, good bonding to a natural biological surface such as a tooth and/or another implant, radio-opacity, excellent long term properties, and good aesthetics. Materials fulfilling one or more of these desirable properties are known in the art and have been described in, e.g., WO 90/11066, EP 559 627 A2, WO 00/21489, WO 01/76534, WO 01/76535, WO 2003/041662, and WO 2004/037215.

Additionally, WO 2005/039508 discloses a two-step system for chemically bonded ceramic (CBC) materials, preferably a dental filling material or an implant material. The system includes an initial working part system to provide for improved early-age properties and a second system to provide for improved end-product properties, including bioactivity. The initial working part system comprises polyacrylic acid and/or a salt or ester thereof, or other polycarboxylic acid, copolymer thereof, or polycarboxylate (i.e., a salt or ester) thereof, and a glass powder. Such an initial working part system is traditionally described as a glass ionomer cement system. The second system is of the hydrating cement system type, in particular, reactive cement-based systems that comprise chemically bonded ceramics of aluminates or silicates. WO 2005/039508 specifically discloses material compositions that provide a hybrid material of calcium aluminate or calcium silicate and glass ionomer cement to form a bioactive dental cement system. However, the prior art system exhibits lower mechanical strength than conventional high strength glass ionomer cement systems and also higher opacity for visible light compared to modern high strength glass ionomer cement systems. Accordingly, further improvements in obtaining a combination of good properties as described above, as well as bioactive features, are desired.

SUMMARY OF THE INVENTION

It is therefore an object of the invention to provide novel cement systems exhibiting a good combination of desirable properties.

In one embodiment, the invention is directed to a cement system for forming an implant, and the cement system comprises a reactive glass ionomer cement (GIC) powder, a polycarboxylic acid or salt or ester thereof, and a filler which is substantially inert when mixed with water and is selected from $(CaO)(Al_2O_3)_6$, $(CaO)(Al_2O_3)_2$, calcium silicate $(CaOSiO_2)$, and mixtures thereof. The substantially inert filler is included in an amount of from about 1 to about 35 wt %, about 3 to about 35 wt %, about 5 to about 30 wt %, or about 10 to about 25 wt %, based on the weight of the GIC powder and the substantially inert filler. The polycarboxylic acid or salt or ester thereof is included in an amount sufficient to initially provide a paste having a pH of less than 7 when the cement system is mixed with water.

In another embodiment, the invention is directed to a cement system for forming an implant, and the cement system comprises a reactive glass ionomer cement (GIC) powder, a polycarboxylic acid or salt or ester thereof, a filler which is substantially reactive when mixed with water and is selected from $(CaO)_2(SiO_2)$, $(CaO)_3(SiO_2)$, and mixtures thereof, and an additional acid. The substantially reactive filler is included in an amount of from about 5 to about 60 wt %, about 10 to about 50 wt %, about 10 to about 40 wt %, or about 10 to about 30 wt %, based on the weight of the GIC powder and the substantially reactive filler. The polycarboxylic acid or salt or ester thereof is included in an amount sufficient to initially provide a paste having a pH of less than 7 when the cement system is mixed with water. The additional acid is included in an amount sufficient to maintain the paste at a pH of less than 7 for at least one hour, at least 2 hours, or at least 3 hours, after the cement system is mixed with water.

In further embodiments, the invention is directed to hardened cements formed from the cement systems of the invention and, more specifically, to hardened cements in the form of implants, including, but not limited to, dental implants.

The cement systems of the present invention advantageously provide hardened glass ionomer cements with bioactive properties, without significantly altering other desirable properties of the GICs. The cement systems are therefore particularly useful in implant applications and, more specifically, in dental implant applications. Additional advantages of the invention will be more fully apparent in view of the following detailed description.

BRIEF DESCRIPTION OF THE DRAWINGS

The detailed description will be more fully understood in view of the drawings in which.

DETAILED DESCRIPTION

The cement systems of the invention include a reactive glass ionomer cement (GIC) powder, a polycarboxylic acid or salt, and a filler. The polycarboxylic acid or salt may be supplied in powder form or as an aqueous suspension or solution. The filler is employed in powder form. The additional acid, when included, may be supplied in powder form or as an aqueous suspension or solution. The powder components of the system are typically referred to as precursor powder, and the precursor powder is mixed with a liquid to form a cement paste. The mixing liquid may contain one or more of the acid component(s) or the one or more of the acid component(s) may be added in one or more separate liquid additions. The cement paste is injected or otherwise placed in a cavity, e.g., a mold or a dental cavity, applied between parts to be cemented together, e.g., a dental crown and a natural tooth, or used in another implant application. The cement paste hardens to form hardened cement.

The cement systems of the invention generally include a ceramic phase in a conventional glass ionomer cement formulation to provide bioactive properties to the hardened cement, particularly at the hardened cement surface. As is well known in the art, glass ionomer cement powder is an acid-soluble calcium fluoroaluminosilicate glass similar to that of silicate but typically has a higher alumina-silicate ratio that increases its reactivity with liquid. Lanthanum, strontium, barium and/or zinc oxide additives maybe included to provide radio-opacity. Typically, the raw materials are fused to form a uniform glass by heating them to temperatures of 1100° C. to 1500° C., and the glass is ground into a powder having particles of a size in the range of less than 100 μm, or, more specifically, 15 to 50 μm. The particles may be sized by, inter alia, sieving. As is also known in the art, the GIC systems employ a polycarboxylic acid or salt or ester thereof, included in an amount sufficient to initially provide a paste having a pH of less than 7 when the cement system is mixed with water. Within the present disclosure, "polycarboxylic acid" includes both polymers and copolymers containing carboxylic functional groups. In a specific embodiment, the weight ratio of polycarboxylic acid or salt or ester thereof to the GIC powder and the filler is in a range of about 0.2-0.6:1. In additional embodiments, the polycarboxylic acid is a polyacrylic acid.

In specific embodiments employing a substantially inert filler, the polycarboxylic acid or salt or ester thereof is included in an amount sufficient to maintain the pH of the cement paste below 7 for at least one hour, at least 2 hours, at least 3 hours, at least 6 hours, or at least 12 hours, after the cement system is mixed with water. In further embodiments, the polycarboxylic acid or salt or ester thereof is included in an amount sufficient to maintain the pH of the cement paste below 7 for at least one day, at least 2 days, or at least 3 days, after the cement system is mixed with water. Optionally, an additional acid as described herein may be added to further maintain the pH of the cement paste below 7 for the desired period of time.

In specific embodiments employing the substantially reactive filler, an additional acid is included in order to maintain the pH of the cement paste below 7 for a desired period of time, for example, at least one hour, at least 2 hours, at least 3 hours, at least 6 hours, at least 12 hours, or at least 24 hours. In further embodiments, the additional acid is included in an amount sufficient to maintain the pH of the cement paste below 7 for at least one day, at least 2 days, or at least 3 days, after the cement system is mixed with water.

According to the present invention, bioactivity is obtained in the GIC system by use of either a substantially inert (i.e., nonreactive) filler or, conversely, by use of a substantially reactive filler, wherein the substantially inert and substantially reactive properties are with respect to mixing the filler with water. In the embodiment employing the substantially inert filler, notwithstanding the fact that the filler does not participate to any noticeable extent in the setting reaction of the cement, the cement is provided with a negative surface charge after setting. The negative surface charge induces the formation of a layer of apatite on the cement surface, providing the implant with improved bioactivity. In embodiments employing the substantially reactive filler, the alkaline setting reaction contributes to the formation of a negative surface charge both during and after setting. Thus, long term bioactive properties of the hardened cement are connected to the formation of a negative surface charge by the filler, while short term bioactive properties are connected to the setting reaction of the reactive filler in which $Ca^{+2}$ and $OH^-$ ions are released. A surface layer of apatite results. Within the present disclosure, bioactivity is measured by the formation of apatite on the hardened cement surface, measured according to ISO 23317, "Implants for surgery—In vitro evaluation for apatite-forming ability of implant materials."

Within the present description, the following abbreviations are employed: C=CaO, A=$Al_2O_3$, and S=$SiO_2$.

The substantially inert filler is selected from $CA_6$ (($CaO$)($Al_2O_3$)$_6$), $CA_2$ (($CaO$)($Al_2O_3$)$_2$), calcium silicate, CS ($CaOSiO_2$), and mixtures thereof. CS may be supplied as wollastonite. These fillers are substantially inert as they are considered to be a non-setting phase and react only slowly with water-based liquids. The substantially inert filler is included in the cement system in an amount of from about 1 to about 35 wt %, about 3 to about 35 wt %, about 5 to about 30 wt %, or about 10 to about 25 wt %, based on the weight of the GIC powder and the substantially inert filler. Amounts of substantially inert filler above about 35 wt % will undesirably reduce the mechanical strength of the dental material since the particles do not actively participate in the setting and hardening. In a specific embodiment employing the substantially inert filler, any significant amount of reactive filler is avoided. Thus, in more specific embodiments, the cement systems containing the substantially inert filler contain less than about 10 wt %, less than about 5 wt %, less than about 1 wt %, or essentially no (i.e., less than about 0.1 wt %), filler which is substantially reactive when mixed with water. Such substantially reactive fillers include $C_{12}A_7$ (($CaO$)$_{12}$($Al_2O_3$)), $C_3A$ (($CaO$)$_3$($Al_2O_3$)), $C_3A$ (($CaO$)$_3$($Al_2O_3$)), $C_2S$ (($CaO$)$_2$($SiO_2$)), $C_3S$ (($CaO$)$_3$($SiO_2$)), and mixtures thereof.

In the embodiment employing the substantially reactive filler, the filler is selected from $C_2S$ (($CaO$)$_2$($SiO_2$)), $C_3S$ ((CaO)$_3$(SiO$_2$)), and mixtures thereof. These phases are substantially reactive in that they are self-setting when mixed with water. These phases will co-react with the glass ionomer system and provide both a release of Ca and OH ions giving an increased pH and a bioactive end product. The substantially reactive filler is included in the cement system in an amount of about 5 to about 60 wt %, about 10 to about 50 wt %, about 10 to about 40 wt %, or about 10 to about 30 wt %, based on the weight of the GIC powder and the substantially reactive filler. An additional acid is included in the cement system employing the substantially reactive filler. The additional acid is included in an amount sufficient to maintain the paste at a pH of less than 7 for at least one hour, at least 2 hours, at least 3 hours, at least 6 hours or at least 12 hours, after the cement system is mixed with water. The additional acid therefore maintains an acidic pH in order to further increase the extent of the setting reaction. In further embodiments, the weight ratio of additional acid to the GIC powder and the substantially reactive filler is in a range of about 0.4-1.0:1, or more specifically, about 0.4-0.8:1. Generally, the higher the content of substantially reactive filler, the higher the content of additional acid which is employed. Any inorganic or organic acid may be employed. In specific embodiments, the additional acid is tartaric acid or citric acid.

The filler may have any desired particle size, but in specific embodiments, the filler has an average particle size less than about 20 μm, less than about 5 μm, or less than about 1 μm. In more specific embodiments, the filler has a maximum particle size less than about 20 μm, less than about 5 μm, or less than about 1 μm. Particle size may be measured by sieving or other well-known techniques.

In additional embodiments, hardened, chemically bonded ceramics may also be added as filler particles to the glass ionomer cement powder. Examples include, but are not limited to, Gibbsite, Katoite, calcium silicate hydrate, and calcium hydroxide. The average particle size of such hardened chemically bonded ceramics is less than about 20 μm, or less than about 5 μm, and these fillers may be added in an amount less than about 35 wt %, less than about 25 wt %, or less than about 20 wt %, based on the weight of the inorganic precursor powder.

The hardened cement is formed by contacting the dry powders with an aqueous liquid to form a paste, delivering the paste to a desired location, and allowing the paste to harden. As described above, the acid components may be pre-suspended or dissolved in an aqueous liquid prior to admixture with the GIC powder and filler. In specific embodiments, the powder to liquid ratio used to form the paste is suitably about 2 to 7, or more specifically about 3 to 5. The aqueous liquid may be further functionalized using various additives; for example, for the reactive calcium silicate phases, CaCl can be added to the aqueous liquid for setting control.

EXAMPLES

The following Examples illustrate non-limiting features of the invention and are not to be interpreted as limiting of any aspect of the invention as disclosed herein.

Example 1

A cement was composed of liquid part, comprising an aqueous solution of tartaric acid (L(+), Sigma-Aldrich), and a powder part. The powder part comprised reactive glass ionomer cement (GIC) powder, reactive calcium silicate (via Portland cement, C$_3$S and C$_2$S) and polyacrylic acid (PAA). The GIC powder was partly replaced by Portland cement as follows: (1) Control group, without Portland cement; (2) Portland cement:(glass+Portland cement)=10 wt %; (3) Portland cement:(glass+Portland cement)=20 wt %; and (4) Portland cement:(glass+Portland cement)=30 wt %. The cement was prepared by mixing the powder part and the liquid part on a plastic pad. More tartaric acid and water were required to form a paste with good consistency when the amount of Portland cement increased. The operation and setting time, compressive strength, pH change and in vitro bioactivity of the cements were evaluated.

Figure 1A:
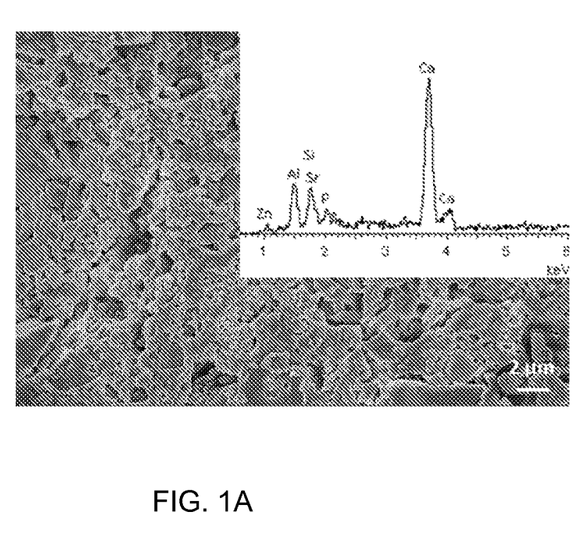
FIGS. 1A and 1B show scanning electron microscope (SEM) micrographs of a hardened cement containing 20 wt % Portland cement after immersion in simulated body fluid (SBF) for one hour and 7 days, respectively, as described in Example 1.
Figure 1B:
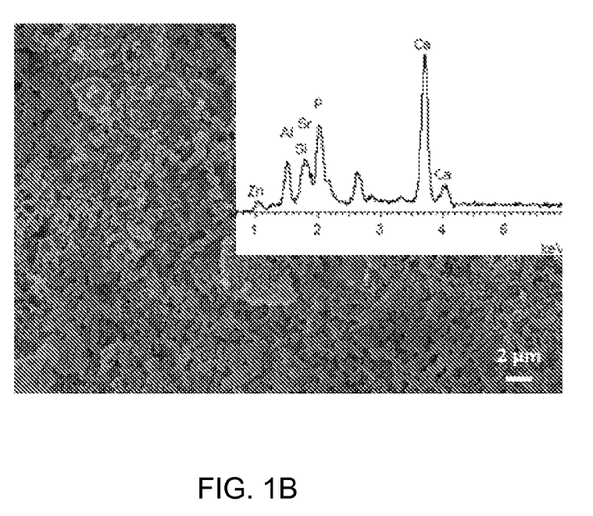

Results: 10 wt % Portland cement had no effect on initial and final setting time of the cement system as compared with the Control. When the amount of Portland cement was further increased to 20 wt % and 30 wt %, the final setting times were prolonged to 12 min and 15 min, respectively (10 min for the non-modified GIC Control). A decrease of compressive strength (18%) was observed with 10 wt % Portland cement. However, no significant difference was seen between 20 wt % Portland cement (65 MPa) and the GIC Control (64 MPa). The incorporation of Portland cement increased the final pH. GIC with 30 wt % Portland cement showed the highest pH value, 7.3 after 7 days. All samples with Portland cement had a new mineralized apatite (hydroxyapatite, HA) layer after 7 days while the GIC Control cement did not demonstrate any HA formation. See FIGS. 1A and 1B, which show scanning electron microscope (SEM) micrographs of the sample containing 20 wt % Portland cement after immersion in simulated body fluid (SBF) for one hour and 7 days, respectively.

Conclusions: Incorporation of a reactive filler, Portland cement, into GIC facilitated the formation of apatite on the surface of the material. The setting time and compressive strength of GIC with 20% of Portland cement were almost the same as non-modified GIC.

Example 2

20 wt % wollastonite (grain size less than 10 μm) was added to the powder part of a glass ionomer cement formulation, i.e., 20 wt % of the GIC powder was replaced with wollastonite. The material was mixed with an aqueous mixing liquid and allowed to harden. The mechanical properties and the bioactivity of the material were tested following ISO 23317. The testing showed that the compressive strength was reduced by about 10% and that the material showed bioactivity, i.e., apatite formation was detected on the hardened cement surface.

Example 3

GIC systems using substantially inert filler comprising wollastonite (CS) and GIC systems using substantially reactive filler comprising a mixture of C$_3$S and C$_2$S (mineral trioxide or MTA, white Portland cement) were formulated. To form the cement paste, an aqueous solution of tartaric acid (L(+)) was employed. For wollastonite modified GIC, (glass+wollastonite): PAA: tartaric acid was 1:0.4:0.6, by wt, and four composition groups were formulated: (1) Control group without wollastonite, (2) CS:glass=10%, (3) CS:glass=20% and (4) CS:glass=30%. For MTA modified GIC, the tartaric acid content was varied up to (glass+MTA): PAA: tartaric acid 1:0.4:0.8, by wt, and four composition groups were formulated: (1) Control group without MTA, (2) MTA: (glass+MTA)=10%, (3) MTA: (glass+MTA)=20% and (4) MTA: (glass+MTA)=30%. The cement was prepared by mixing the powder and liquid part on a plastic pad using stainless spatula.

Initial and final setting times were determined by the Gillmore needles. Compressive strength was measured using a cylinder 4 mm in diameter and 6 mm in height and a universal testing machine (Autograph AGS-X, Shimadzu) with a crosshead speed of 1 mm/min. The pH change in water and in SBF solution was measured on samples with diameter of 8 mm and thickness of 1 mm immersed in 5 ml of SBF and water, respectively, for 7 days using a pH meter. The original SBF (pH=7.4) served as control. Surface bioactivity was evaluated using surface morphology (SEM LEO 1550), and energy-dispersive X-ray spectroscopy (EDS) elemental analysis was used to further characterize the surface composition of hardened cements.

The initial and final setting times of the GIC with and without wollastonite and MTA are given in Tables 1 and 2. The addition of wollastonite only slightly affected the initial setting time. When increasing the amount of wollastonite, the final setting time remained the same. 10% MTA did not affect initial and final setting time of the GIC. By further increasing the amount of MTA, the consistency of the cements became worse. In order to obtain good consistency, more tartaric acid and water were required. When the amount of MTA was up to 30%, 30% tartaric acid solution was required and the ratio of glass: MTA: PAA was 1:0.4:0.8 in order to form a good paste. In this case, the initial and final setting times were prolonged to 10 min and 15 min, respectively.

TABLE 1

Initial and final setting times for wollastonite modified cements

| Cement | Initial setting time(min) | Final setting time(min) |
|---|---|---|
| GIC | 4 | 10 |
| 10% wollastonite | 5 | 10 |
| 20% wollastonite | 5 | 10 |
| 30% wollastonite | 5 | 10 |

TABLE 2

Initial and final setting times for MTA modified cements

| Cement | Concentration of tartaric acid | Glass:MTA:PAA (weight ratio) | Initial setting time(min) | Final setting time(min) |
|---|---|---|---|---|
| GIC | 10% | 1:0.4:0.6 | 4 | 10 |
| 10% MTA | 10% | 1:0.4:0.6 | 4 | 11 |
| 20% MTA | 10% | 1:0.4:0.6 | — | — |
| 20% MTA | 20% | 1:0.4:0.6 | 4 | 12 |
| 30% MTA | 20% | 1:0.4:0.6 | — | — |
| 30% MTA | 20% | 1:0.4:0.8 | — | — |
| 30% MTA | 30% | 1:0.4:0.8 | 10 | 15 |

Figure 2:
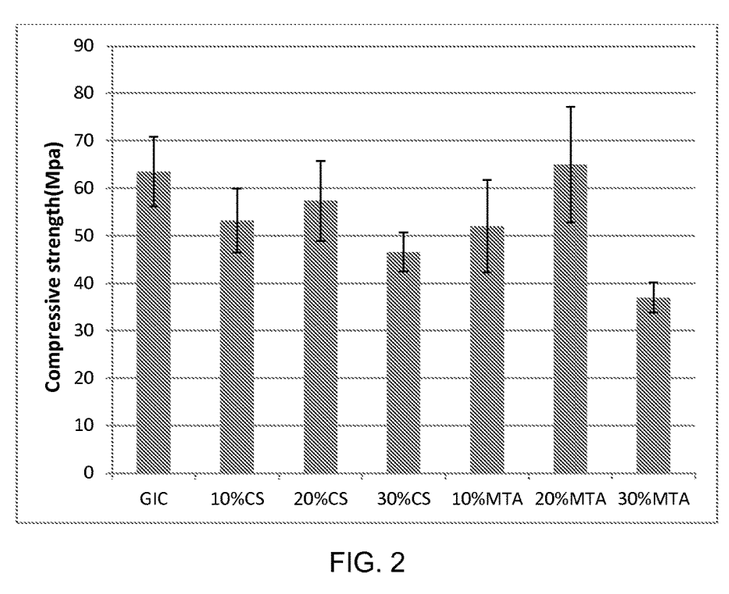
FIG. 2 shows compressive strength of samples as described in Example 3.

The addition of wollastonite in the GIC resulted in slightly decreased compressive strength, see FIG. 2. The incorporation of 10% and 20% wollastonite resulted in 17% and 11% decrease in compressive strength. The compressive strength of the cement with 30% wollastonite (47 Mpa) was lower than that of the 10% and 20% wollastonite (p<0.05). The addition of 10% MTA resulted in a decrease (18%) of compressive strength (p<0.05). No significant difference could be observed between control group (64 MPa) and 20% MTA (65 MPa). The compressive strength decreased to 37 MPa when 30% MTA was added.

Figure 3A:
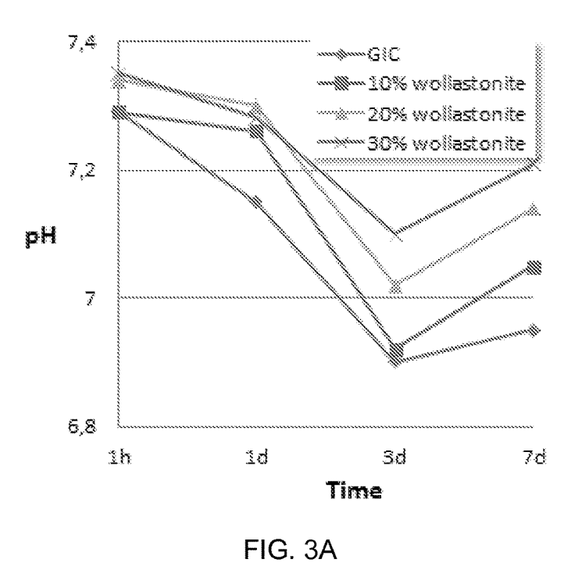
FIGS. 3A-3D show pH changes in samples in water and simulated body fluid (SBF) as described in Example 3.
Figure 3B:
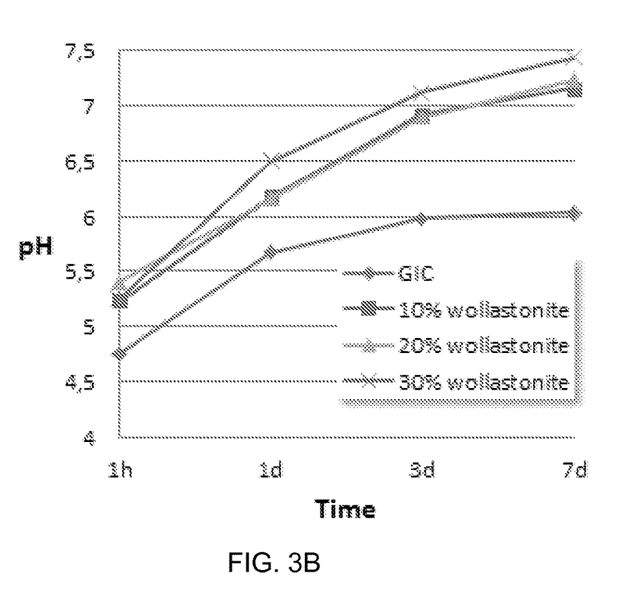
Figure 3C:
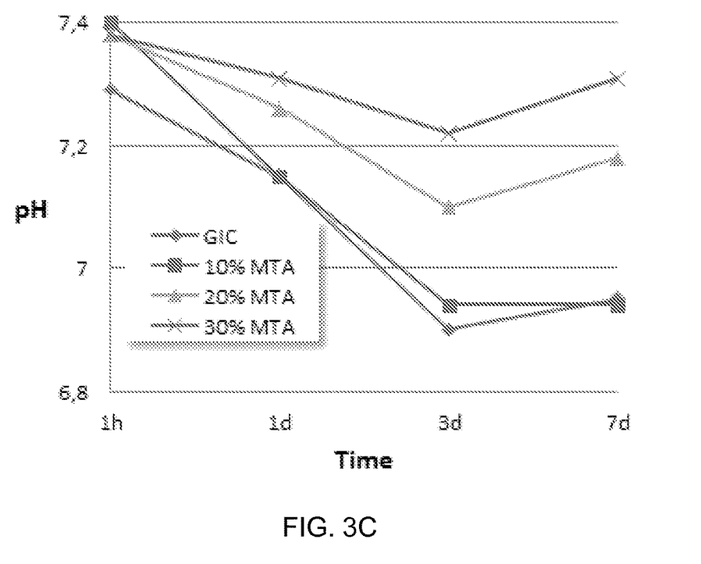
Figure 3D:
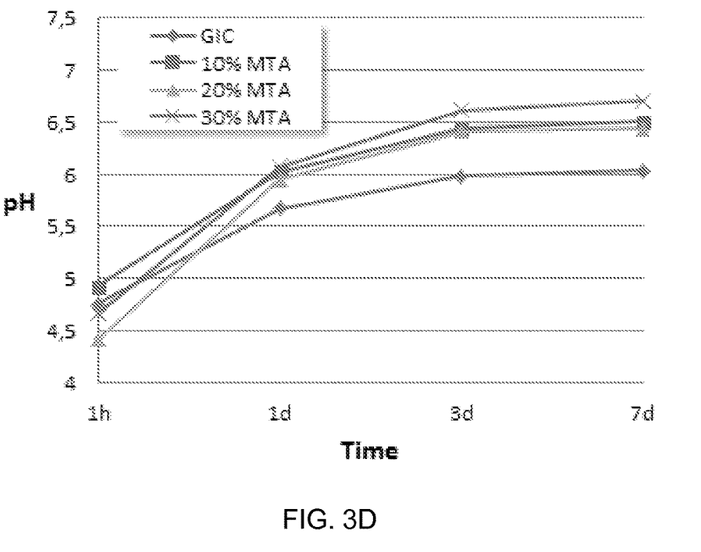

The pH values in SBF are shown in FIGS. 3A and 3C and the pH values in water are shown in FIGS. 3B and 3D. All groups showed a decrease in pH after immersion in distilled water for the first one hour. Then the pH values started to increase after 1 h. After 7 days immersion in distilled water, the pH values of the group with pure GIC reached a stable value of approximate 6. For GIC incorporating 10%, 20%, and 30% wollastonite, the pH values were 7.16, 7.23, and 7.43 respectively. In SBF, the pH for all cements decreased during the first 3 days and then increased. For the GIC control, the pH was less than 7 after 7 days. The pH increased with addition of wollastonite and MTA. For 30% wollastonite-modified GIC, the pH did not vary over time, and the pH was higher than that of 10% and 20% wollastonite, close to 7.3 after 7days. GIC with 30% MTA showed the highest pH value, 7.3, after 7 days as compared with 10% and 20% MTA.

Figure 4:
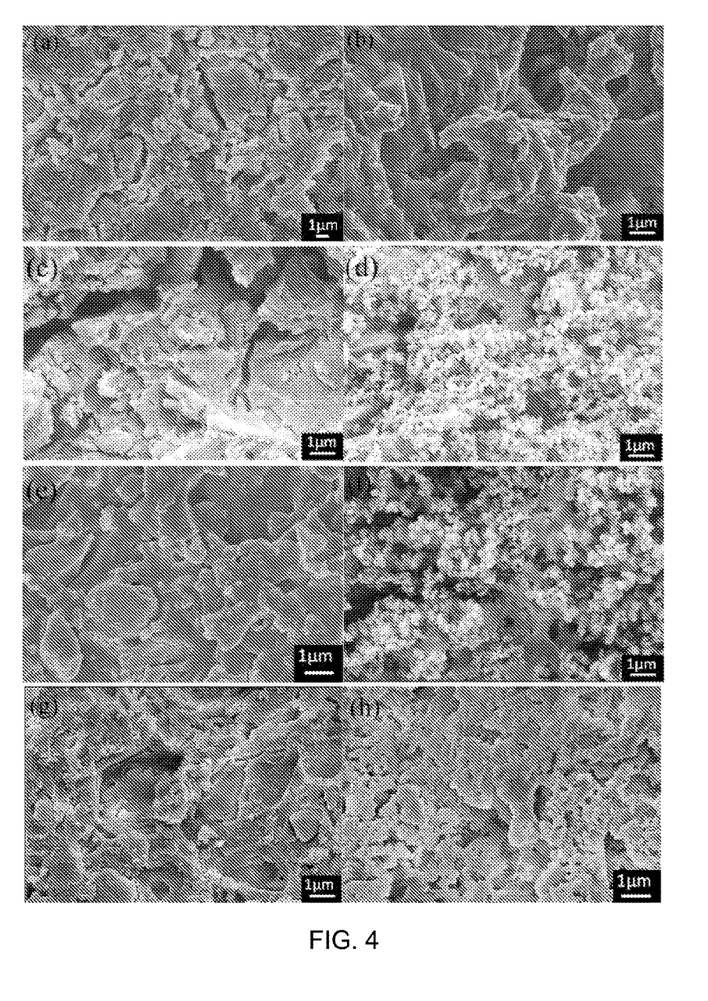
FIG. 4 shows surface morphology of samples as described in Example 3.
Figure 5:
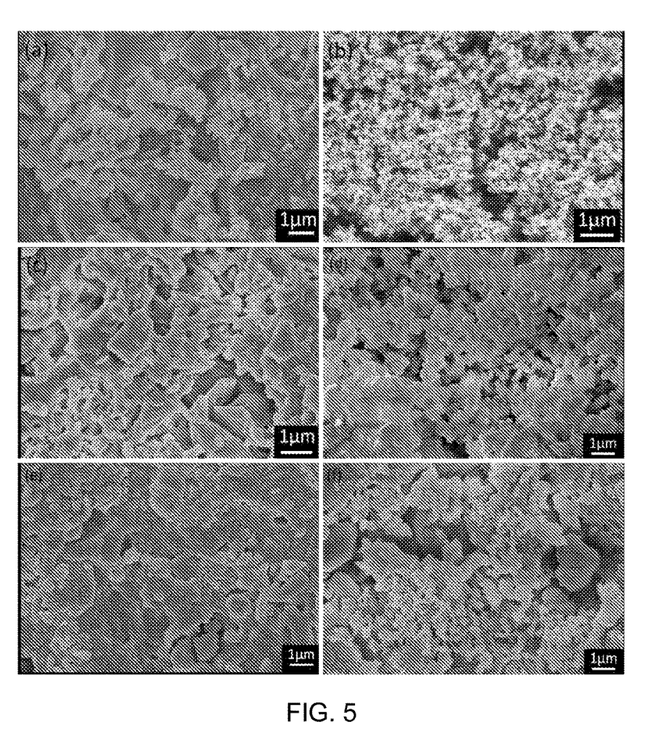
FIG. 5 shows surface morphology of samples as described in Example 3.
Figure 6A:
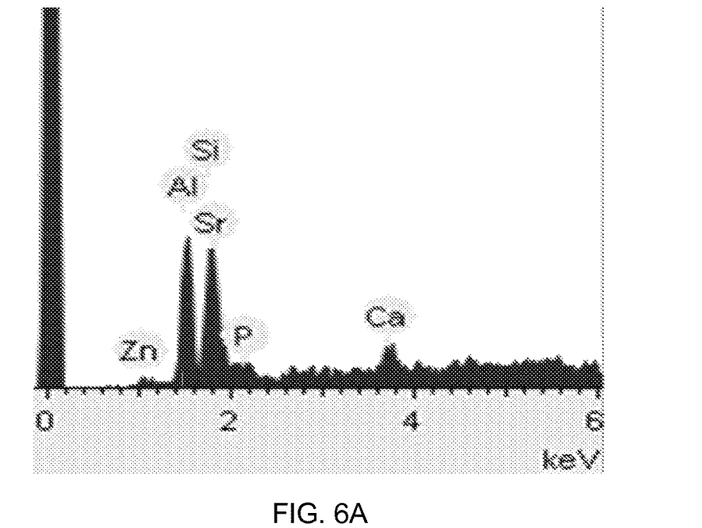
FIGS. 6A-6C show the results of energy-dispersive X-ray spectroscopy (EDS) analyses of samples as described in Example 3.
Figure 6B:
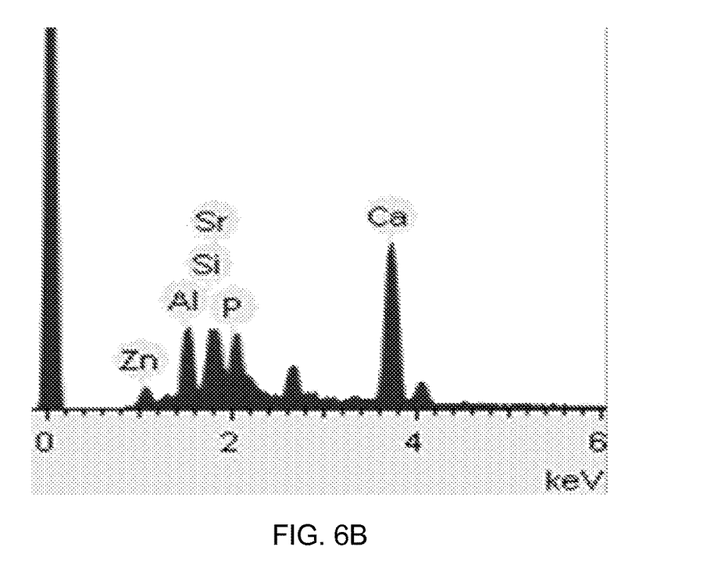
Figure 6C:
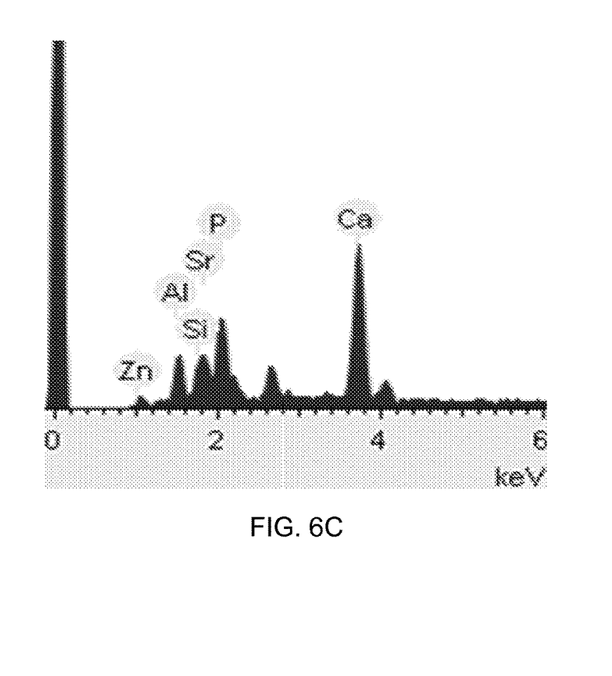

The GIC control surfaces were similar after both 1 h and 7 days soaking, see FIG. 4, panels (a) and (b). The samples containing wollastonite and MTA had the same surface morphology as the GIC control initially, see FIG. 4, panels (c), (e) and (g), and FIG. 5, panels (a), (c) and (e). But the wollastonite and MTA samples showed a new mineralized layer after 7 days, see FIG. 4, panels (d), (f) and (h), and FIG. 5, panels (b), (d) and (f). EDS analyses of a GIC control surface and surfaces of GIC containing 20 wt % wollastonite and MTA, respectively, as shown in FIGS. 6A-6C revealed the presence of Ca, Si, Sr, Al and Zn, and, in GIC containing 20 wt % wollastonite and MTA, respectively (FIGS. 7B and 7C), a significantly higher P peak, evidencing a bioactive apatite layer.

Example 4

Figure 7:
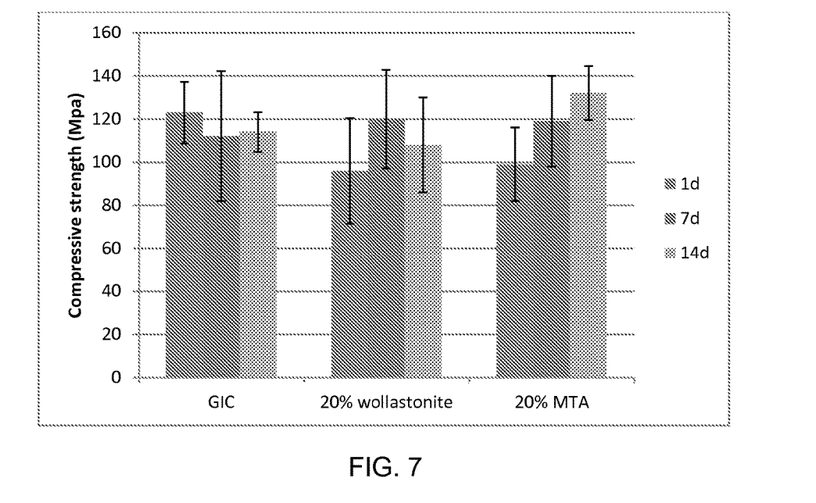
FIG. 7 shows surface morphology of samples as described in Example 4.

Samples of a commercial GIC (Batch number: 101321-4, glass ionomer luting cement, Advanced Health Care Ltd, UK) were modified with wollastonite and MTA, respectively. 20% of the glass powder was replaced by wollastonite or MTA. Setting time, compressive strength (1 day, 7 days and 14 days) and bioactivity in SBF solution were studied. The methods were generally as described in Example 3. After one day, the compressive strength with 20% wollastonite (96 Mpa) and 20% MTA (99 Mpa) were lower than the GIC control (122 Mpa) (p<0.05), as shown in FIG. 7. After storage for more than one day, the strength increased and no significant difference could be found for the GIC control and GIC with 20 wt % wollastonite, while the compressive strength of GIC with 20 wt % MTA increased even further after 14 days (132 Mpa) (p<0.05). After 14 days, the compressive strength of GIC with 20 wt % MTA was higher than GIC control and GIC with 20 wt % wollastonite (p<0.05).

Figure 8:
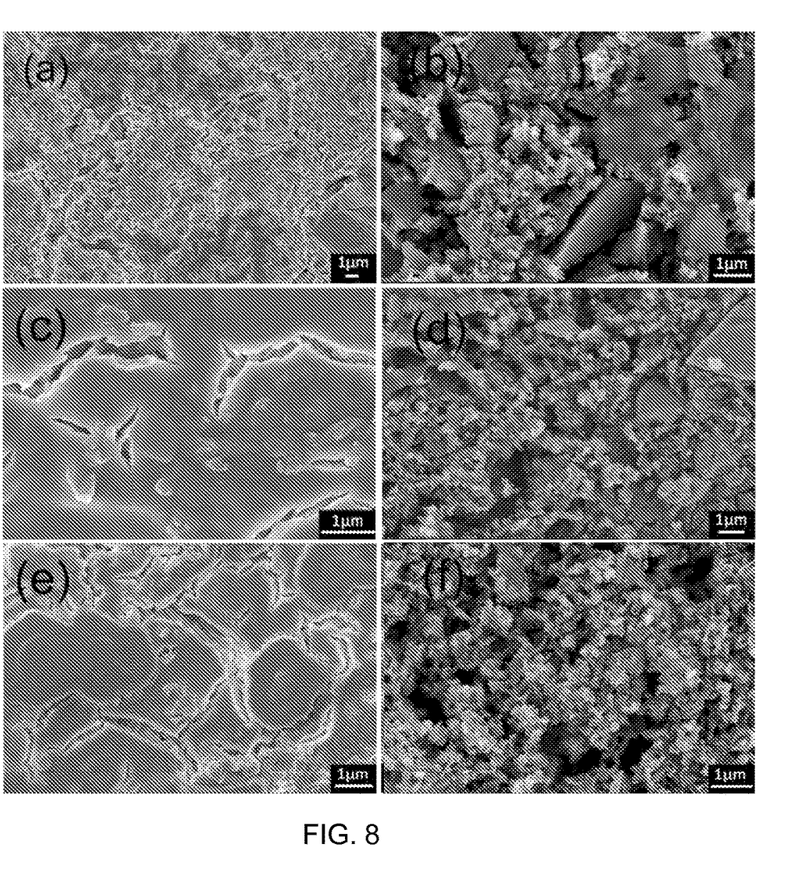
FIG. 8 shows surface morphology of samples as described in Example 4.
Figure 9A:
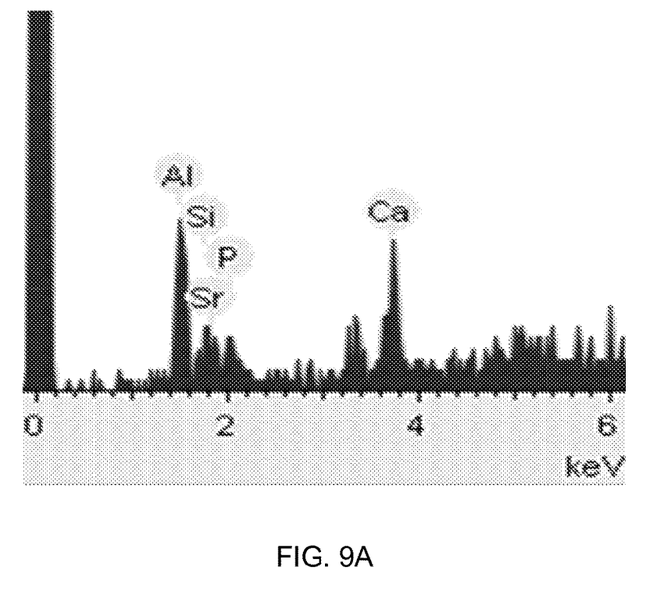
FIGS. 9A-9C show the results of EDS analyses of samples as described in Example 4.
Figure 9B:
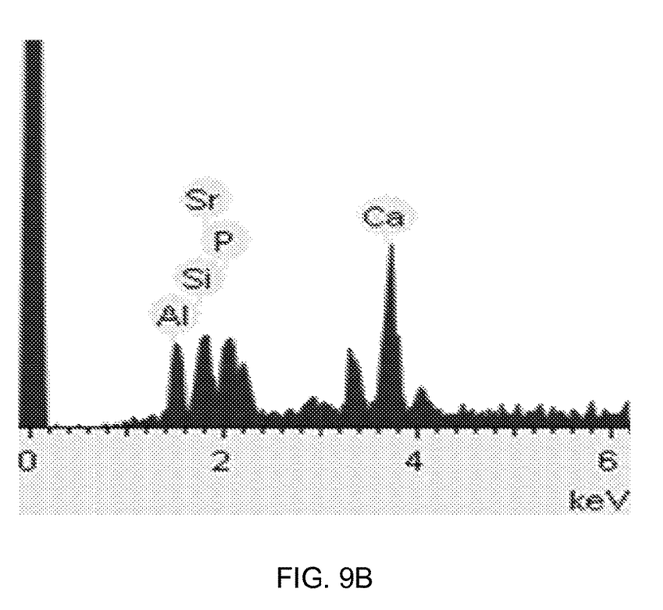
Figure 9C:
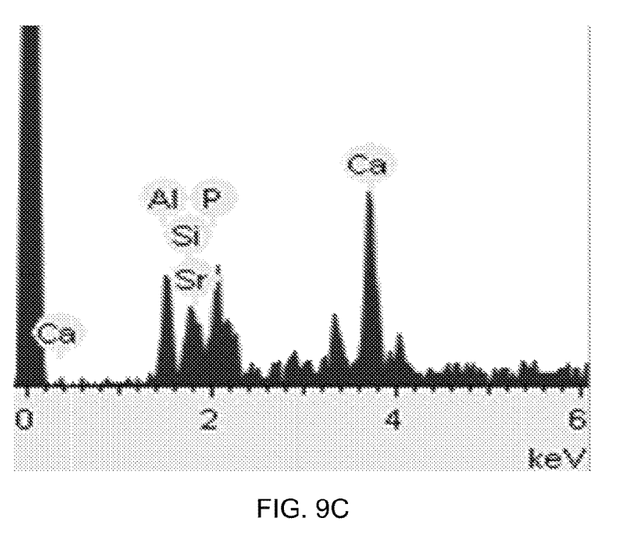

Apatite formation was observed on the surfaces of the test groups with calcium silicates after 14 days, as shown in FIG. 8 in which panels (a), (c) and (e) show the surface of the GIC control, GIC with 20 wt % wollastonite and GIC with 20 wt % MTA, respectively, all after 1 hour in SBF, and panels (b), (d) and (f) show the surface of the GIC control, GIC with 20 wt % wollastonite and GIC with 20 wt % MTA, respectively, all after 14 days in SBF. The EDS spectra showed that the amount of phosphate on the surface of GIC with 20 wt % wollastonite, FIG. 9B, and GIC with 20 wt % MTA, FIG. 9C, respectively, were higher compared with GIC control group, FIG. 9A.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification, embodiments and examples be considered as exemplary only, with a true scope and spirit of the invention being indicated by the following claims.

What is claimed is:

1. A cement system for forming an implant, comprising a reactive glass ionomer cement (GIC) powder, a polycarboxylic acid or salt or ester thereof, and a filler which is substantially inert when mixed with water and is selected from $(CaO)(Al_2O_3)_6$, $(CaO)(Al_2O_3)_2$, calcium silicate $(CaOSiO_2)$, and mixtures thereof, wherein the substantially inert filler is included in an amount of from about 1 to about 35 wt %, based on the weight of the GIC powder and the substantially inert filler, and the polycarboxylic acid or salt or ester thereof is included in an amount sufficient to initially provide a paste having a pH of less than 7 when the cement system is mixed with water and to maintain the pH of the cement paste below 7 for at least one hour after the cement system is mixed with water.

2. The cement system of claim 1, wherein the substantially inert filler is Wollastonite.

3. The cement system of claim 1, wherein the substantially inert filler is $(CaO)(Al_2O_3)_6$, $(CaO)(Al_2O_3)_2$, or a mixture thereof.

4. The cement system of claim 1, containing less than about 10 wt % of a filler which is substantially reactive when mixed with water and is selected from $(CaO)_{12}(Al_2O_3)_7$, $(CaO)(Al_2O_3)$, $(CaO)_3(Al_2O_3)$, $(CaO)_2(SiO_2)$, $(CaO)_3(SiO_2)$, and mixtures thereof.

5. The cement system of claim 1, wherein the polycarboxylic acid or salt or ester thereof is included in an amount sufficient to maintain the pH of the cement paste below 7 for at least 2 hours after the cement system is mixed with water.

6. The cement system of claim 1, wherein the weight ratio of polycarboxylic acid or salt or ester thereof to the GIC powder and the filler is in a range of about 0.2-0.6:1.

7. The cement system of claim 1, wherein the filler has an average particle size less than about 20 µm.

8. The cement system of claim 1, wherein the polycarboxylic acid or salt or ester thereof is polyacrylic acid.

9. A hardened cement implant formed by mixing the cement system of claim 1 with water, wherein the hardened cement has a bioactive layer of apatite at its surface.

10. The implant of claim 9, in the form of a dental implant.

11. The implant of claim 10, wherein the implant is adapted to be cemented to another implant and/or a natural tooth.

12. The cement system of claim 1, further comprising an additional acid.

13. The cement system of claim 12, wherein the additional acid is tartaric acid or citric acid.

14. A cement system for forming an implant, comprising a reactive glass ionomer cement (GIC) powder, a polycarboxylic acid or salt or ester thereof, a filler which is substantially reactive when mixed with water and is selected from $(CaO)_2(SiO_2)$, $(CaO)_3(SiO_2)$, and mixtures thereof, and an additional acid, wherein the substantially reactive filler is included in an amount of from about 5 to about 60 wt %, based on the weight of the GIC powder and the substantially reactive filler, the polycarboxylic acid or salt or ester thereof is included in an amount sufficient to initially provide a paste having a pH of less than 7 when the cement system is mixed with water, and the additional acid is included in an amount sufficient to maintain the paste at a pH of less than 7 for at least one hour after the cement system is mixed with water.

15. The cement system of claim 14, wherein the substantially reactive filler is Portland cement comprising $(CaO)_2(SiO_2)$ and $(CaO)_3(SiO_2)$.

16. The cement system of claim 14, wherein the additional acid is tartaric acid or citric acid.

17. The cement system of claim 16, wherein the substantially reactive filler is Portland cement comprising $(CaO)_2(SiO_2)$ and $(CaO)_3(SiO_2)$.

18. The cement system of claim 16, wherein the weight ratio of additional acid to the GIC powder and the substantially reactive filler is in a range of about 0.4-0.8:1.

19. The cement system of claim 16, wherein the weight ratio of polycarboxylic acid or salt or ester thereof to the GIC powder and the filler is in a range of about 0.2-0.6:1.

20. The cement system of claim 16, wherein the filler has an average particle size less than about 20 µm.

21. The cement system of claim 16, wherein the polycarboxylic acid or salt or ester thereof is polyacrylic acid.

22. A hardened cement implant formed by mixing the cement system of claim 16 with water, wherein the hardened cement has a bioactive layer of apatite at its surface.

23. The implant of claim 22, in the form of a dental implant.

24. The cement system of claim 14, wherein the weight ratio of additional acid to the GIC powder and the substantially reactive filler is in a range of about 0.4-0.8:1.

25. The cement system of claim 14, wherein the weight ratio of polycarboxylic acid or salt or ester thereof to the GIC powder and the filler is in a range of about 0.2-0.6:1.

26. The cement system of claim 14, wherein the filler has an average particle size less than about 20 µm.

27. The cement system of claim 14, wherein the polycarboxylic acid or salt or ester thereof is polyacrylic acid.

28. A hardened cement implant formed by mixing the cement system of claim 14 with water, wherein the hardened cement has a bioactive layer of apatite at its surface.

29. The implant of claim 28, in the form of a dental implant.

* * * * *

UNITED STATES PATENT AND TRADEMARK OFFICE
CERTIFICATE OF CORRECTION

PATENT NO. : 10,292,791 B2
APPLICATION NO. : 15/324314
DATED : May 21, 2019
INVENTOR(S) : Håkan Engqvist It is certified that error appears in the above-identified patent and that said Letters Patent is hereby corrected as shown below:

On the Title Page

Item (30), change "1400345" to --1400345-3--.

Signed and Sealed this
Ninth Day of July, 2019

Andrei Iancu
*Director of the United States Patent and Trademark Office*